US010849561B2

United States Patent
Huang et al.

(10) Patent No.: US 10,849,561 B2
(45) Date of Patent: Dec. 1, 2020

(54) SYSTEMS AND METHODS FOR REDUCING RESPIRATORY-INDUCED MOTION ARTIFACTS FOR ACCELERATED IMAGING

(71) Applicant: University of Virginia Patent Foundation, Charlotlesville, VA (US)

(72) Inventors: Wei Huang, Charlottesville, VA (US); Yang Yang, Charlottesville, VA (US); Xiao Chen, Charlottesville, VA (US); Michael Salerno, Charlottesville, VA (US)

(73) Assignee: University of Virginia Patent Foundation, Charlottesville, VA (US)

(*) Notice: Subject to any disclaimer, the term of this patent is extended or adjusted under 35 U.S.C. 154(b) by 546 days.

(21) Appl. No.: 15/331,292

(22) Filed: Oct. 21, 2016

(65) Prior Publication Data

US 2017/0112449 A1    Apr. 27, 2017

Related U.S. Application Data

(60) Provisional application No. 62/244,555, filed on Oct. 21, 2015.

(51) Int. Cl.
*A61B 5/00* (2006.01)
*A61B 5/055* (2006.01)
(Continued)

(52) U.S. Cl.
CPC .......... *A61B 5/7207* (2013.01); *A61B 5/0044* (2013.01); *A61B 5/055* (2013.01);
(Continued)

(58) Field of Classification Search
CPC ..... A61B 17/3403; A61B 34/10; A61B 34/20; A61B 5/7207; A61B 5/0044; A61B 5/055;
(Continued)

(56) References Cited

U.S. PATENT DOCUMENTS 7,174,200 B2    2/2007 Salerno et al.
8,700,127 B2    4/2014 Salerno et al.
(Continued)

FOREIGN PATENT DOCUMENTS

WO    02084305 A2    10/2002

OTHER PUBLICATIONS

Pruessmann, K.P., et al., "SENSE: Sensitivity Encoding for Fast MRI," Magn. Reson. Med., 1999, vol. 42, pp. 952-962.
(Continued)

*Primary Examiner* — Malina D. Blaise
(74) *Attorney, Agent, or Firm* — Meunier Carlin & Curfman LLC

(57) ABSTRACT

In some aspects, the disclosed technology relates to reducing respiratory-induced motion artifacts for accelerated imaging. In one embodiment, magnetic resonance data may be acquired for an area of a subject containing the heart. The acquired data may include motion-corrupted data due to respiration of the subject. From the acquired data, an image may be independently reconstructed for each of a plurality of time frames, with each time frame corresponding to one of a plurality of heartbeats. A region containing the heart of the subject may be automatically detected in the reconstructed images, and rigid motion registration may be performed on the region of the reconstructed images containing the heart. Based on the rigid motion registration, a linear phase shift for motion correction may be determined. The linear phase shift may be applied to the motion-corrupted data to produce linear phase-shifted data, and a k-t image reconstruction may be performed on the linear phase-shifted data to produce motion-corrected images.

23 Claims, 7 Drawing Sheets

(51) Int. Cl.
*G01R 33/565* (2006.01)
*A61B 5/113* (2006.01)
*G01R 33/561* (2006.01)

(52) U.S. Cl.
CPC ........ *A61B 5/113* (2013.01); *G01R 33/56509* (2013.01); *G01R 33/5611* (2013.01)

(58) Field of Classification Search
CPC .............. A61B 5/113; G01R 33/56509; G01R 33/5611
See application file for complete search history.

(56) References Cited

U.S. PATENT DOCUMENTS

| | | | | |
|---|---|---|---|---|
| 8,823,374 | B2* | 9/2014 | Weller | G01R 33/5611 324/307 |
| 9,224,210 | B2 | 12/2015 | Epstein et al. | |
| 2006/0226836 | A1* | 10/2006 | Shu | G01R 33/56509 324/309 |
| 2007/0025524 | A1* | 2/2007 | Yue | A61N 5/1049 378/205 |
| 2009/0010514 | A1* | 1/2009 | Kimura | G06T 5/50 382/131 |
| 2009/0087057 | A1* | 4/2009 | Parker | G01R 33/56509 382/131 |
| 2012/0081114 | A1* | 4/2012 | Weller | G01R 33/5611 324/309 |
| 2013/0279786 | A1* | 10/2013 | Lin | G01R 33/5611 382/131 |
| 2013/0307536 | A1 | 11/2013 | Feng et al. | |
| 2013/0315461 | A1* | 11/2013 | Zhao | G06T 7/0012 382/131 |
| 2014/0219531 | A1* | 8/2014 | Epstein | G01R 33/56308 382/131 |
| 2015/0077112 | A1* | 3/2015 | Otazo | A61B 5/055 324/318 |
| 2016/0104279 | A1* | 4/2016 | Li | A61B 5/055 382/131 |
| 2016/0148378 | A1 | 5/2016 | Salerno et al. | |
| 2016/0334487 | A1* | 11/2016 | Bieri | G01R 33/50 |
| 2016/0341810 | A1* | 11/2016 | Rich | G01R 33/5608 |

OTHER PUBLICATIONS

Griswold, M.A., et al. "Generalized Autocalibrating Partially Parallel Acquisitions (GRAPPA)," Magn. Reson. Med., 2002 vol. 47, pp. 1202-1210.
Lustig, M., et al., "SPIRiT: Iterative Self-Consistent Parallel Imaging Reconstruction From Arbitrary k-Space," Magn. Reson. Med., 2010, vol. 64, pp. 457-471.
Tsao, J., et al., "k-t BLAST and k-t SENSE: Dynamic MRI With High Frame Rate Exploiting Spatiotemporal Correlations," Magn. Reson. Med., 2003, vol. 50, pp. 1031-1042.
Pedersen, H., et al., "k-t PCA: Temporally Constrained k-t BLAST Reconstruction Using Principal Component Analysis," Magn. Reson. Med., 2009, vol. 62, pp. 706-716.
Schmidt, J.F., et al., "Iterative k-t Principal Component Analysis With Nonrigid Motion Correction for Dynamic Three Dimensional Cardiac Perfusion Imaging," Magn. Reson. Med., 2013, 12 pages.
Lingala, S.G., et al., "Accelerated Dynamic MRI Exploiting Sparsity and Low-Rank Structure: k-t SLR," IEEE Trans. Med. Imag., 2011, vol. 30, No. 5, pp. 1042-1054.
Yang, Y., et al., "First-Pass Myocardial Perfusion Imaging With Whole-Heart Coverage Using L1-SPIRiT Accelerated Variable Density Spiral Trajectories," Magn. Reson. Med., 2015, 13 pages.
Wang, Y., et al., "Navigator-Echo-Based Real-Time Respiratory Gating and Triggering for Reduction of Respiration Effects in Three-Dimensional Coronary MR Angiography," Radiology, 1996, vol. 198, pp. 55-60.
Usman, M. et al., "Motion Corrected Compressed Sensing for Free-Breathing Dynamic Cardiac MRI," Magn. Reson. Med., 2013, vol. 70, pp. 504-516.
Thévanaz, P., et al., "Interpolation Revisited," IEEE Trans. Med. Imaging, 2000, vol. 19, No. 7, pp. 739-758.
Wissmann, L., et al., "MRXCAT: Realistic Numerical Phantoms for Cardiovascular Magnetic Resonance," J. Cardiovasc. Magn. Reson., 2014, vol. 16, 11 pages.
Ehman et al., "Adaptive Technique for High Definition MR Imaging of Moving Structures," Radiology 1989, vol. 173, pp. 255-263.
Larson et al., "Self-Gated Cardiac Cine MRI," Magn. Reson. Med., 2004, vol., 51, pp. 93-102.

* cited by examiner

SYSTEMS AND METHODS FOR REDUCING RESPIRATORY-INDUCED MOTION ARTIFACTS FOR ACCELERATED IMAGING

CROSS-REFERENCE TO RELATED APPLICATIONS

This Application claims priority to, and benefit under 35 U.S.C. §119(e) of, U.S. Provisional Patent Application No. 62/244,555, filed Oct. 21, 2015, which is hereby incorporated by reference herein in its entirety as if fully set forth below.

STATEMENT OF RIGHTS UNDER FEDERALLY-SPONSORED RESEARCH

This invention was made with government support under grant K23 HL112910-01, awarded by the National Institutes of Health. The government has certain rights in this invention.

BACKGROUND

Cardiac magnetic resonance (CMR) perfusion imaging has significant advantages for cardiac stress testing, including high diagnostic accuracy for detecting coronary artery disease. Current clinical techniques, however, only acquire three or four slices during a heartbeat with limited spatial and temporal resolution ([1-3]). K-space over time (k-t) accelerated techniques provide a powerful tool for reducing the amount of data acquired during imaging. Specifically, known k-t accelerated techniques, such as k-t sensitivity encoding (SENSE) ([4]) and k-t principal component analysis (PCA) ([5,6]), utilize temporal correlations in dynamic data to constrain image reconstruction. Although these techniques can achieve high acceleration factors, they are sensitive to motion (e.g. respiratory motion) as these methods assume that a subject is not changing or moving with respect to time. Therefore, images acquired using k-t accelerated techniques often have motion-induced artifacts caused by movement that can obscure a subject's relevant features Like k-t accelerated techniques, compressed sensing techniques ([7]) enable highly accelerated acquisition. However, compressed sensing techniques are also sensitive to respiratory motion, which can cause image blurring. Examples of compressed sensing techniques for dynamic imaging series, such as myocardial perfusion imaging, include L1-SPIRIT ([3,8]) and K-t SLR ([7]). On the other hand, navigator gating based techniques ([9]), used primarily for free breathing-coronary imaging, prolong image acquisition time, require dedicated setup, and are prone to errors due to the difference between diaphragmatic motion and cardiac motion.

Known self correction strategies ([10]) extract motion information from acquired data and then use the extracted information during image reconstruction. There has been significant interest and development in using non-rigid registration techniques to correct for cardiac and respiratory motion. However, these techniques are not robust enough for routine clinical application in k-t-accelerated CMR perfusion imaging. Additionally, repeated application of non-rigid registration operators can result in image degradation due to repeated spatial interpolation ([11]).

It is with respect to these and other considerations that the various aspects of the disclosed technology as described below are presented.

SUMMARY

In some aspects, the disclosed technology relates to reducing respiratory-induced motion artifacts for accelerated imaging. In some embodiments, magnetic resonance data may be acquired for an area of a subject containing the heart. The acquired data may include motion-corrupted data due to respiration of the subject. From the acquired data, an image may be independently reconstructed for each of a plurality of time frames, with each time frame corresponding to one of a plurality of heartbeats. A region containing the heart of the subject may be automatically detected in the reconstructed images, and rigid motion registration may be performed on the region of the reconstructed images containing the heart. Based on the rigid motion registration, a linear phase shift for motion correction may be determined. The linear phase shift may be applied to the motion-corrupted data to produce linear phase-shifted data, and a k-t image reconstruction may be performed on the linear phase-shifted data to produce motion-corrected images.

In one embodiment, the disclosed technology relates to a method which includes acquiring magnetic resonance data for an area of a subject containing the heart, where the acquired magnetic resonance data includes motion-corrupted data due to respiration of the subject. The method also includes reconstructing, from the acquired magnetic resonance data, an image for each time frame of a plurality of time frames, where each time frame corresponds to a single heartbeat of a plurality of heartbeats of the subject and each respective image is reconstructed independently. The method also includes automatically detecting, in the reconstructed images, a region containing the heart of the subject, and performing rigid motion registration on the region of the reconstructed images containing the heart. The method also includes determining a linear phase shift for motion correction based on the rigid motion registration, applying the linear phase shift to the acquired magnetic resonance data with the motion-corrupted data to produce linear phase-shifted data, and performing a k-t image reconstruction on the linear phase-shifted data to produce motion-corrected images.

Each respective image may be reconstructed independently such as to avoid temporal blurring in images used for image registration. The reconstructing, from the acquired magnetic resonance data, of an image for each time frame of the plurality of time frames may include parallel image reconstruction. The parallel image reconstruction may include iterative self-consistent parallel image reconstruction (SPIRiT).

Performing rigid registration on the region of the reconstructed images containing the heart may include performing registration in the image domain or k-space domain. Determining, based on the rigid registration, the linear phase shift may include deriving linear k-space shifts in the x and y direction.

Acquiring the magnetic resonance data may include performing k-t accelerated acquisition. Performing the k-t image reconstruction on the linear phase-shifted data to produce motion-corrected images may include k-t exploiting sparsity and low rank structure (k-t SLR), k-t principal component analysis (k-t PCA), or k-t PCA with sensitivity encoding (SENSE).

The magnetic resonance data may be acquired during free-breathing of the subject or continuous data acquisition in multiple phases of the cardiac cycle of the heart of the subject. The magnetic resonance data may be acquired using a Cartesian, radial, or spiral k-space trajectory. Acquiring the magnetic resonance data may include incoherent sampling, and the k-t image reconstruction may include compressed sensing reconstruction exploiting sparsity in the temporal direction.

In another embodiment, the disclosed technology relates to a system which includes a data acquisition device configured to acquire magnetic resonance data for an area of a subject containing the heart, where the acquired magnetic resonance data includes motion-corrupted data due to respiration of the subject. The system also includes one or more processors coupled to the data acquisition device and configured to cause the system to perform specific functions. The specific functions include reconstructing, from the acquired magnetic resonance data, an image for each time frame of a plurality of time frames, where each time frame corresponds to a single heartbeat of a plurality of heartbeats of the subject, and each respective image is reconstructed independently. The specific functions also include automatically detecting, in the reconstructed images, a region containing the heart of the subject, and performing rigid motion registration on the region of the reconstructed images containing the heart. The specific functions also include determining, based on the rigid motion registration, a linear phase shift for motion correction, applying the linear phase shift to the acquired magnetic resonance data with the motion-corrupted data to produce linear phase-shifted data, and performing a k-t image reconstruction on the linear phase-shifted data to produce motion-corrected images.

Each respective image may be reconstructed independently such as to avoid temporal blurring in images used for image registration. The reconstructing, from the acquired magnetic resonance data, of an image for each time frame of the plurality of time frames may include parallel image reconstruction. The parallel image reconstruction may include iterative self-consistent parallel image reconstruction (SPIRiT).

Performing rigid registration on the region of the reconstructed images containing the heart may include performing registration in the image domain or k-space domain. Determining, based on the rigid registration, the linear phase shift may include deriving linear k-space shifts in the x and y direction.

Acquiring the magnetic resonance data may include performing k-t accelerated acquisition. Performing the k-t image reconstruction on the linear phase-shifted data to produce motion-corrected images may include k-t exploiting sparsity and low rank structure (k-t SLR), k-t principal component analysis (k-t PCA), or k-t PCA with sensitivity encoding (SENSE).

The magnetic resonance data may be acquired during free-breathing of the subject or continuous data acquisition in multiple phases of the cardiac cycle of the heart of the subject. The magnetic resonance data may be acquired using a Cartesian, radial, or spiral k-space trajectory. Acquiring the magnetic resonance data may include incoherent sampling, and the k-t image reconstruction may include compressed sensing reconstruction exploiting sparsity in the temporal direction.

In yet another embodiment, the disclosed technology relates to a non-transitory computer-readable medium having stored instructions that, when executed by one or more processors, cause a computing device to perform specific functions. The specific functions include acquiring magnetic resonance data for an area of a subject containing the heart, where the acquired magnetic resonance data includes motion-corrupted data due to respiration of the subject. The specific functions also include reconstructing, from the acquired magnetic resonance data, an image for each time frame of a plurality of time frames, where each time frame corresponds to a single heartbeat of a plurality of heartbeats of the subject, and each respective image is reconstructed independently. The specific functions also include automatically detecting, in the reconstructed images, a region containing the heart of the subject, and performing rigid motion registration on the region of the reconstructed images containing the heart. The specific functions also include determining, based on the rigid motion registration, a linear phase shift for motion correction, applying the linear phase shift to the acquired magnetic resonance data with the motion-corrupted data to produce linear phase-shifted data, and performing a k-t image reconstruction on the linear phase-shifted data to produce motion-corrected images.

Each respective image may be reconstructed independently such as to avoid temporal blurring in images used for image registration. The reconstructing, from the acquired magnetic resonance data, of an image for each time frame of the plurality of time frames may include parallel image reconstruction. The parallel image reconstruction may include iterative self-consistent parallel image reconstruction (SPIRiT).

Performing rigid registration on the region of the reconstructed images containing the heart may include performing registration in the image domain or k-space domain. Determining, based on the rigid registration, the linear phase shift may include deriving linear k-space shifts in the x and y direction.

Acquiring the magnetic resonance data may include performing k-t accelerated acquisition. Performing the k-t image reconstruction on the linear phase-shifted data to produce motion-corrected images may include k-t exploiting sparsity and low rank structure (k-t SLR), k-t principal component analysis (k-t PCA), or k-t PCA with sensitivity encoding (SENSE).

The magnetic resonance data may be acquired during free-breathing of the subject or continuous data acquisition in multiple phases of the cardiac cycle of the heart of the subject. The magnetic resonance data may be acquired using a Cartesian, radial, or spiral k-space trajectory. Acquiring the magnetic resonance data may include incoherent sampling, and the k-t image reconstruction may include compressed sensing reconstruction exploiting sparsity in the temporal direction.

Other aspects and features according to the example embodiments of the disclosed technology will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale.

DETAILED DESCRIPTION

Figure 1:
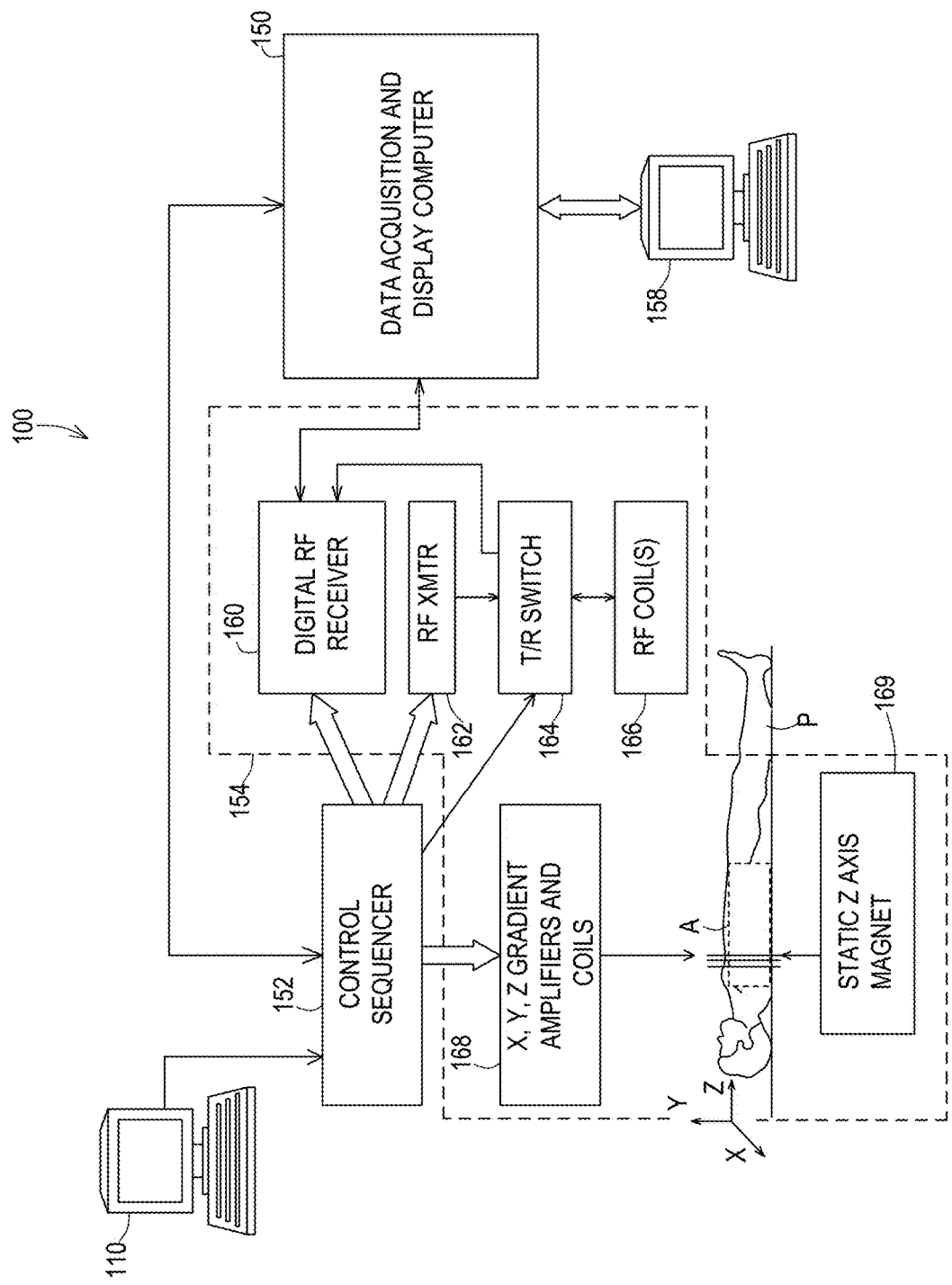
FIG. 1 is a system diagram illustrating an imaging system capable of implementing aspects of the disclosed technology in accordance with one or more example embodiments.

In some aspects, the disclosed technology relates to a simple and robust motion-compensation strategy for selectively correcting respiratory-induced artifacts using rigid motion registration. Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

As discussed herein, a "subject" (or "patient") may be any applicable human, animal, or other organism, living or dead, or other biological or molecular structure or chemical environment, and may relate to particular components of the subject, for instance specific organs, tissues, or fluids of a subject, may be in a particular location of the subject, referred to herein as an "area of interest" or a "region of interest."

Some references, which may include various patents, patent applications, and publications, are cited in a reference list and discussed in the disclosure provided herein. The citation and/or discussion of such references is provided merely to clarify the description of the disclosed technology and is not an admission that any such reference is "prior art" to any aspects of the disclosed technology described herein. In terms of notation, "[n]" corresponds to the $n^{th}$ reference in the list. For example, [3] refers to the $3^{rd}$ reference in the list, namely Lustig M, Pauly J M. SPIRiT: Iterative self-consistent parallel imaging reconstruction from arbitrary k-Space. Magn Reson Med. 2010; 64: 457-71. All references cited and discussed in this specification are incorporated herein by reference in their entireties and to the same extent as if each reference was individually incorporated by reference.

A detailed description of aspects of the disclosed technology, in accordance with various example embodiments, will now be provided with reference to the accompanying drawings. The drawings form a part hereof and show, by way of illustration, specific embodiments and examples. In referring to the drawings, like numerals represent like elements throughout the several figures.

FIG. 1 is a system diagram illustrating an operating environment capable of implementing aspects of the disclosed technology in accordance with one or more example embodiments. FIG. 1 illustrates an example of a magnetic resonance imaging (MRI) system 100, including a data acquisition and display computer 150 coupled to an operator console 110, an MRI real-time control sequencer 152, and an MRI subsystem 154. The MRI subsystem 154 may include XYZ magnetic gradient coils and associated amplifiers 168, a static Z-axis magnet 169, a digital RF transmitter 162, a digital RF receiver 160, a transmit/receive switch 164, and RF coil(s) 166. The MRI subsystem 154 may be controlled in real time by control sequencer 152 to generate magnetic and radio frequency fields that stimulate magnetic resonance phenomena in a subject P to be imaged, for example, to implement magnetic resonance imaging sequences in accordance with various example embodiments of the disclosed technology described herein. An image of an area of interest A of the subject P (which may also be referred to herein as a "region of interest") may be shown on display 158. The display 158 may be implemented through a variety of output interfaces, including a monitor, printer, or data storage.

The area of interest A corresponds to a region associated with one or more physiological activities in subject P. The area of interest shown in the example embodiment of FIG. 1 corresponds to a chest region of subject P, but it should be appreciated that the area of interest for purposes of implementing various aspects of the disclosure presented herein is not limited to the chest area. It should be recognized and appreciated that the area of interest in various embodiments may encompass various areas of subject P associated with various physiological characteristics, such as, but not limited to the heart region. Physiological activities that may be evaluated by methods and systems in accordance with various embodiments of the disclosed technology may include, but are not limited to cardiac activity and conditions.

It should be appreciated that any number and type of computer-based medical imaging systems or components, including various types of commercially available medical imaging systems and components, may be used to practice certain aspects of the disclosed technology. Systems as described herein with respect to example embodiments are not intended to be specifically limited to magnetic resonance imaging (MRI) implementations or the particular system shown in FIG. 1.

One or more data acquisition or data collection steps as described herein in accordance with one or more embodiments may include acquiring, collecting, receiving, or otherwise obtaining data such as imaging data corresponding to an area of interest. By way of example, data acquisition or collection may include acquiring data via a data acquisition device, receiving data from an on-site or off-site data acquisition device or from another data collection, storage, or processing device. Similarly, data acquisition or data collection devices of a system in accordance with one or more embodiments of the disclosed technology may include any device configured to acquire, collect, or otherwise obtain data, or to receive data from a data acquisition device within the system, an independent data acquisition device located on-site or off-site, or another data collection, storage, or processing device.

Figure 2:
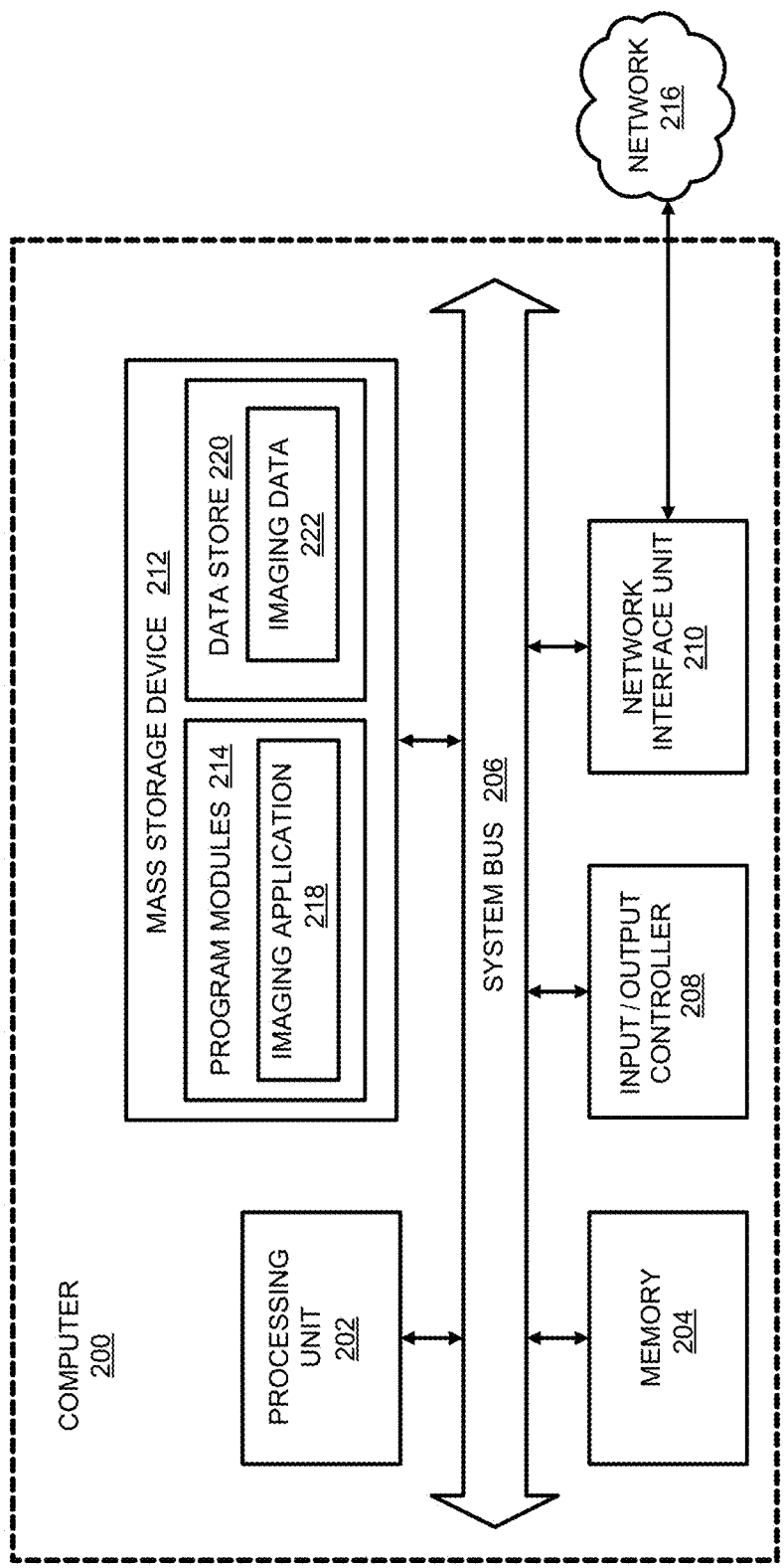
FIG. 2 is a computer architecture diagram showing a general computing system capable of implementing aspects of the disclosed technology in accordance with one or more example embodiments.

FIG. 2 is a computer architecture diagram showing a general computing system capable of implementing aspects of the disclosed technology in accordance with one or more embodiments described herein. A computer 200 may be configured to perform one or more functions associated with embodiments illustrated in one or more of FIGS. 3-7. For example, the computer 200 may be configured to perform various aspects of reducing respiratory-induced motion artifacts for accelerated imaging in accordance with example embodiments, such as magnetic resonance imaging data acquisition, image reconstruction, automatic detection of a region of interest, rigid registration, determining and applying a linear phase shift, and producing motion-corrected images. It should be appreciated that the computer 200 may be implemented within a single computing device or a computing system formed with multiple connected computing devices. The computer 200 may be configured to perform various distributed computing tasks, in which processing and/or storage resources may be distributed among the multiple devices. The data acquisition and display computer 150 and/or operator console 110 of the system shown in FIG. 1 may include one or more systems and components of the computer 200.

As shown, the computer 200 includes a processing unit 202 ("CPU"), a system memory 204, and a system bus 206 that couples the memory 204 to the CPU 202. The computer 200 further includes a mass storage device 212 for storing program modules 214. The program modules 214 may be operable to perform associated with embodiments illustrated in one or more of FIGS. 3-7 discussed below. The program modules 214 may include an imaging application 218 for performing data acquisition and/or processing functions as described herein, for example to acquire and/or process image data corresponding to magnetic resonance imaging of an area of interest. The computer 200 can include a data store 220 for storing data that may include imaging-related data 222 such as acquired data from the implementation of magnetic resonance imaging in accordance with various embodiments of the disclosed technology.

The mass storage device 212 is connected to the CPU 202 through a mass storage controller (not shown) connected to the bus 206. The mass storage device 212 and its associated computer-storage media provide non-volatile storage for the computer 200. Although the description of computer-storage media contained herein refers to a mass storage device, such as a hard disk or CD-ROM drive, it should be appreciated by those skilled in the art that computer-storage media can be any available computer storage media that can be accessed by the computer 200.

By way of example and not limitation, computer storage media (also referred to herein as "computer-readable storage medium" or "computer-readable storage media") may include volatile and non-volatile, removable and non-removable media implemented in any method or technology for storage of information such as computer-storage instructions, data structures, program modules, or other data. For example, computer storage media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the computer 200. "Computer storage media", "computer-readable storage medium" or "computer-readable storage media" as described herein do not include transitory signals.

According to various embodiments, the computer 200 may operate in a networked environment using connections to other local or remote computers through a network 216 via a network interface unit 210 connected to the bus 206. The network interface unit 210 may facilitate connection of the computing device inputs and outputs to one or more suitable networks and/or connections such as a local area network (LAN), a wide area network (WAN), the Internet, a cellular network, a radio frequency (RF) network, a Bluetooth-enabled network, a Wi-Fi enabled network, a satellite-based network, or other wired and/or wireless networks for communication with external devices and/or systems. The computer 200 may also include an input/output controller 208 for receiving and processing input from any of a number of input devices. Input devices may include one or more of keyboards, mice, stylus, touchscreens, microphones, audio capturing devices, and image/video capturing devices. An end user may utilize the input devices to interact with a user interface, for example a graphical user interface, for managing various functions performed by the computer 200. The bus 206 may enable the processing unit 202 to read code and/or data to/from the mass storage device 212 or other computer-storage media. The computer-storage media may represent apparatus in the form of storage elements that are implemented using any suitable technology, including but not limited to semiconductors, magnetic materials, optics, or the like. The computer-storage media may represent memory components, whether characterized as RAM, ROM, flash, or other types of technology.

The computer storage media may also represent secondary storage, whether implemented as hard drives or otherwise. Hard drive implementations may be characterized as solid state, or may include rotating media storing magnetically-encoded information. The program modules 214, which include the imaging application 218, may include instructions that, when loaded into the processing unit 202 and executed, cause the computer 200 to provide functions associated with one or more example embodiments and implementations illustrated in FIGS. 3-7. The program modules 214 may also provide various tools or techniques by which the computer 200 may participate within the overall systems or operating environments using the components, flows, and data structures discussed throughout this description.

In general, the program modules 214 may, when loaded into the processing unit 202 and executed, transform the processing unit 202 and the overall computer 200 from a general-purpose computing system into a special-purpose computing system. The processing unit 202 may be constructed from any number of transistors or other discrete circuit elements, which may individually or collectively assume any number of states. More specifically, the processing unit 202 may operate as a finite-state machine, in response to executable instructions contained within the program modules 214. These computer-executable instructions may transform the processing unit 202 by specifying how the processing unit 202 transitions between states, thereby transforming the transistors or other discrete hardware elements constituting the processing unit 202. Encoding the program modules 214 may also transform the physical structure of the computer-storage media. The specific transformation of physical structure may depend on various factors, in different implementations of this description. Examples of such factors may include, but are not limited to the technology used to implement the computer-storage media, whether the computer storage media are characterized as primary or secondary storage, and the like. For example, if the computer storage media are implemented as semiconductor-based memory, the program modules 214 may transform the physical state of the semiconductor memory, when the software is encoded therein. For example, the program modules 214 may transform the state of transistors, capacitors, or other discrete circuit elements constituting the semiconductor memory.

As another example, the computer storage media may be implemented using magnetic or optical technology. In such implementations, the program modules 214 may transform the physical state of magnetic or optical media, when the software is encoded therein. These transformations may include altering the magnetic characteristics of particular locations within given magnetic media. These transformations may also include altering the physical features or characteristics of particular locations within given optical media, to change the optical characteristics of those locations. Other transformations of physical media are possible without departing from the scope of the present description, with the foregoing examples provided only to facilitate this discussion.

Further details of certain example embodiments of the disclosed technology will now be discussed.

In accordance with some example embodiments, the disclosed technology can enable selective motion-compensation in a region of interest through derivation of linear k-space phase shifts using rigid motion registration. The described motion-compensation techniques can be particularly applicable in imaging of the heart (such as CMR perfusion), especially imaging utilizing k-t accelerated techniques or compressed sensing techniques when a subject is breathing. As perfusion images are acquired in a single phase within the cardiac cycle, the predominant intra-frame motion is due to bulk respiratory motion, which is predominantly rigid. As it turns out, rigid deformations can be robustly estimated using rigid motion registration of a heart region. In some example embodiments, by using the Fourier shift theorem, raw image data can be phase-shifted in k-space, following the rigid deformations estimated using rigid motion registration prior to k-t reconstruction. Incorporating rigid motion registration to derive linear phase shifts and correct motion-induced artifacts can limit repeated spatial interpolation, which may cause image blurring.

Figure 3:
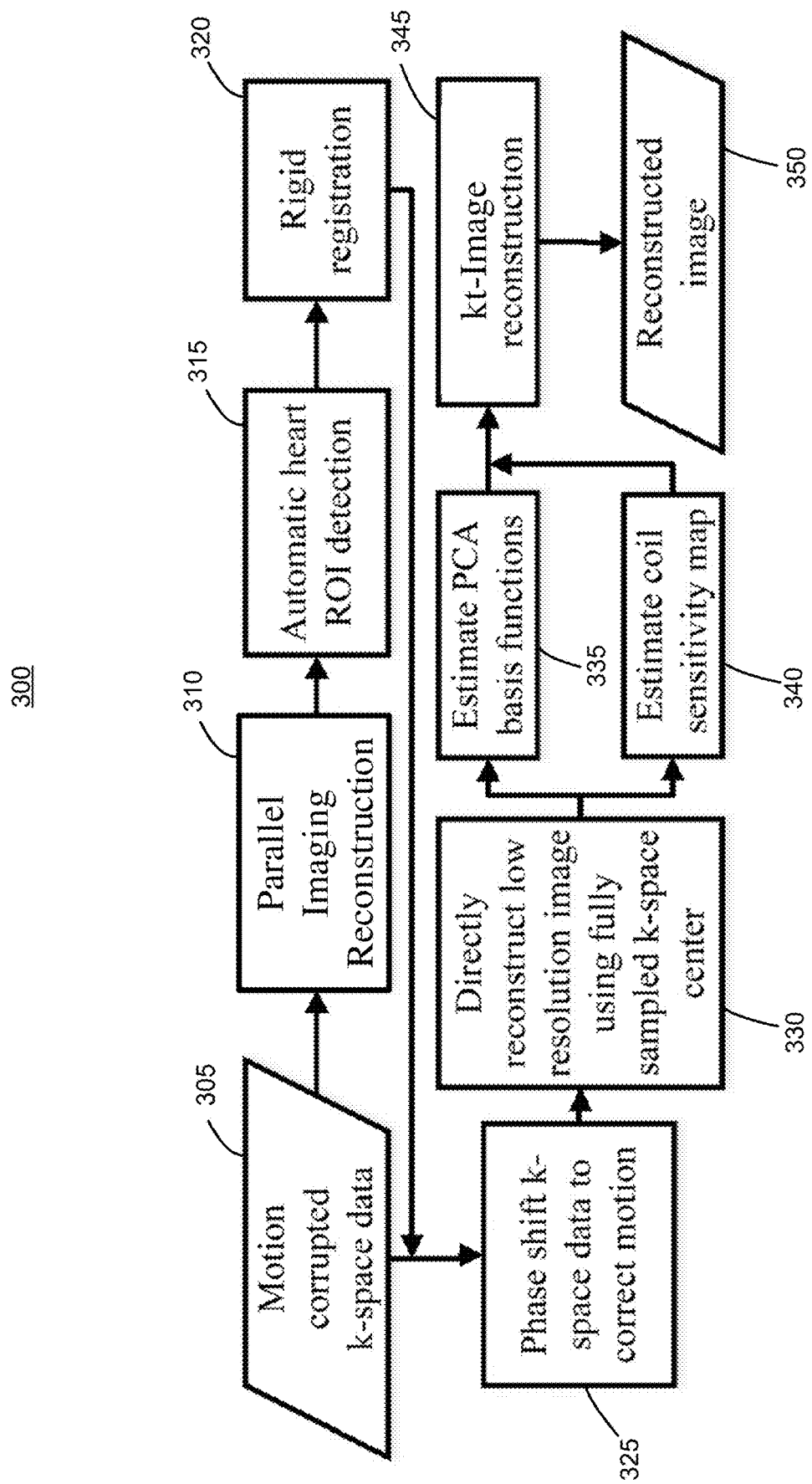
FIG. 3 is a block diagram illustrating a method for reducing respiratory-induced motion artifacts for CMR perfusion imaging in accordance with one example embodiment.

FIG. 3 illustrates a method 300 for reducing respiratory-induced motion artifacts in k-t accelerated CMR perfusion imaging, in accordance with an example embodiment of the disclosed technology. At 305, magnetic resonance data from a subject is acquired over time, for example with one image at each slice location in each heartbeat of a 30-60 second acquisition. In some embodiments, the acquired magnetic resonance data is motion-corrupted magnetic resonance data. When data is acquired during each heartbeat, the subject may be breathing or improperly holding their breath, which can corrupt at least a portion of the magnetic resonance data and create one or more respiratory-induced artifacts, visible in a series of reconstructed images.

From the acquired magnetic resonance data, at 310 a plurality of images of the subject can be reconstructed using a parallel imaging reconstruction technique. In some embodiments, parallel image reconstruction may include using a reconstruction technique, such as iterative self-consistent parallel image reconstruction (SPIRiT). Respective images are reconstructed independently from one another. Independent reconstruction (i.e., not relying on temporal correlation between successive images) of respective images limits blurring, which can occur with k-t image reconstruction.

At 315, a heart region can be automatically detected. The automatic detection can include taking the standard deviation of the image and detecting the signal intensities of the contrasted image to identify a region of interest, such as the heart cavity. In some embodiments, automatic detection can comprise automatically detecting a rectangular region of interest.

Once the heart region is automatically detected at 315, rigid motion registration of the heart region can be performed, at 320. Rigid motion registration can include aligning one or more respective images and estimating the displacement between the one or more respective images. From the estimated displacement, one or more linear phase shifts in the x and y directions can be derived. The one or more linear phase shifts can be applied to the motion-corrupted magnetic resonance data, at 325. In some embodiments, the linear phase shifts can be applied to all the magnetic resonance data acquired of a subject. Phase-shifting all of the magnetic resonance data, using phase shifts derived from a region around the heart can reduce motion artifacts in the heart region despite blurring of irrelevant areas around the region. Motion-corrected low resolution images can be directly reconstructed (see 330) and the low resolution images can be used for calibration of coil sensitivity, reconstruction kernels, or training data, in cases such as k-t PCA where explicit training data is used for the reconstruction (see, e.g., 335 and 340).

In some embodiments, and as seen at FIG. 3, motion-corrected images can be reconstructed from the phase-shifted data using a k-t accelerated imaging technique. It should be appreciated that that the described motion compensation technique can be used with a variety of accelerated imaging techniques, including but not limited to compressed sensing imaging, e.g., k-t exploiting sparsity and low rank structure (k-t SLR), and k-t accelerated techniques, such as k-t principal component analysis (k-t PCA), or k-t PCA with sensitivity encoding (SENSE).

In embodiments specifically incorporating k-t PCA or k-t PCA with SENSE, as illustrated at FIG. 3, data may be trained to estimate the PCA basis functions used for reconstruction (see 335) and sensitivity maps (see 340) can be acquired from the magnetic resonance data for use in image reconstruction, at 345. Using the estimated PCA basis functions and sensitivity maps, an image can be reconstructed using k-t PCA and SENSE (see 345 and 350). It will be appreciated that in certain embodiments, such as embodiments incorporating compressed sensing, such as k-t SLR, images may be reconstructed directly from the phase-shifted magnetic resonance data without estimating PCA basis functions and/or estimating a coil sensitivity map.

EXAMPLE IMPLEMENTATIONS AND RESULTS

Various aspects of the disclosed technology may be still more fully understood from the following description of example implementations and corresponding results and the images of FIGS. 4-7. Some experimental data are presented herein for purposes of illustration and should not be construed as limiting the scope of the disclosed technology in any way or excluding any alternative or additional embodiments.

METHODS

Phantom Studies

A MRXCAT phantom was imaged utilizing k-t PCA with motion correction and k-t SLR with motion correction ([12]). A 4× accelerated variable density k-t sampling pattern was used to fully sample the central 24 lines while under-sampling the remaining lines following a Poisson disk distribution. K-t PCA with motion correction and k-t SLR with motion correction (MC) were performed in accordance with methods described above with respect to certain aspects of FIG. 3. Additionally, k-t PCA and k-t SLR without motion correction were performed for comparison.

Figure 4:
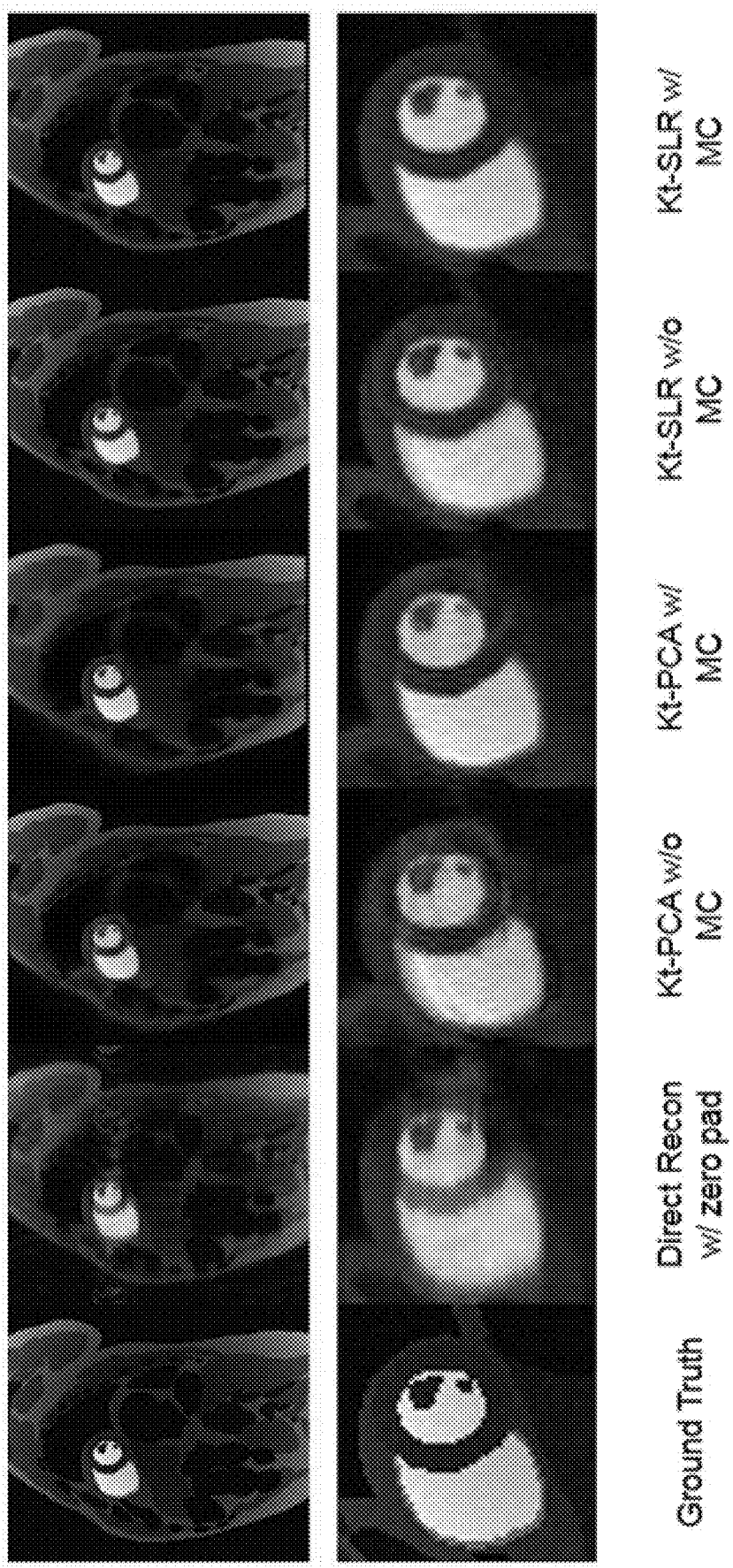
FIG. 4 shows k-t PCA and k-t exploiting sparsity and low rank structure (k-t SLR) reconstructed images of a phantom with and without motion compensation (MC).

FIG. 4 shows various k-t PCA and k-t SLR reconstructed images with and without motion compensation of a phantom. The top row of images shows reconstructed images of the entire body cavity of the phantom at one time frame, while the bottom row of images shows specifically the heart region of interest at one time frame.

Retrospective Reconstruction

The efficacy of k-t PCA with motion correction and k-t SLR with motion correction was verified using retrospective reconstruction. Multi-slice 2D saturation-recovery first-pass perfusion imaging was performed on 4 patients on a 1.5 T scanner with a standard body-phased array RF coil. For each patient, fully sampled magnetic resonance data was acquired. The fully sampled magnetic resonance data was retrospectively subjected to 4× under-sampling following a Poisson disc distribution with 14 center lines. Image reconstruction was performed using both k-t PCA and k-t SLR with the motion-compensation strategies described with respect to FIG. 3. To verify the effectiveness of the described motion compensation techniques, data was reconstructed using k-t PCA without motion compensation.

Figure 5:
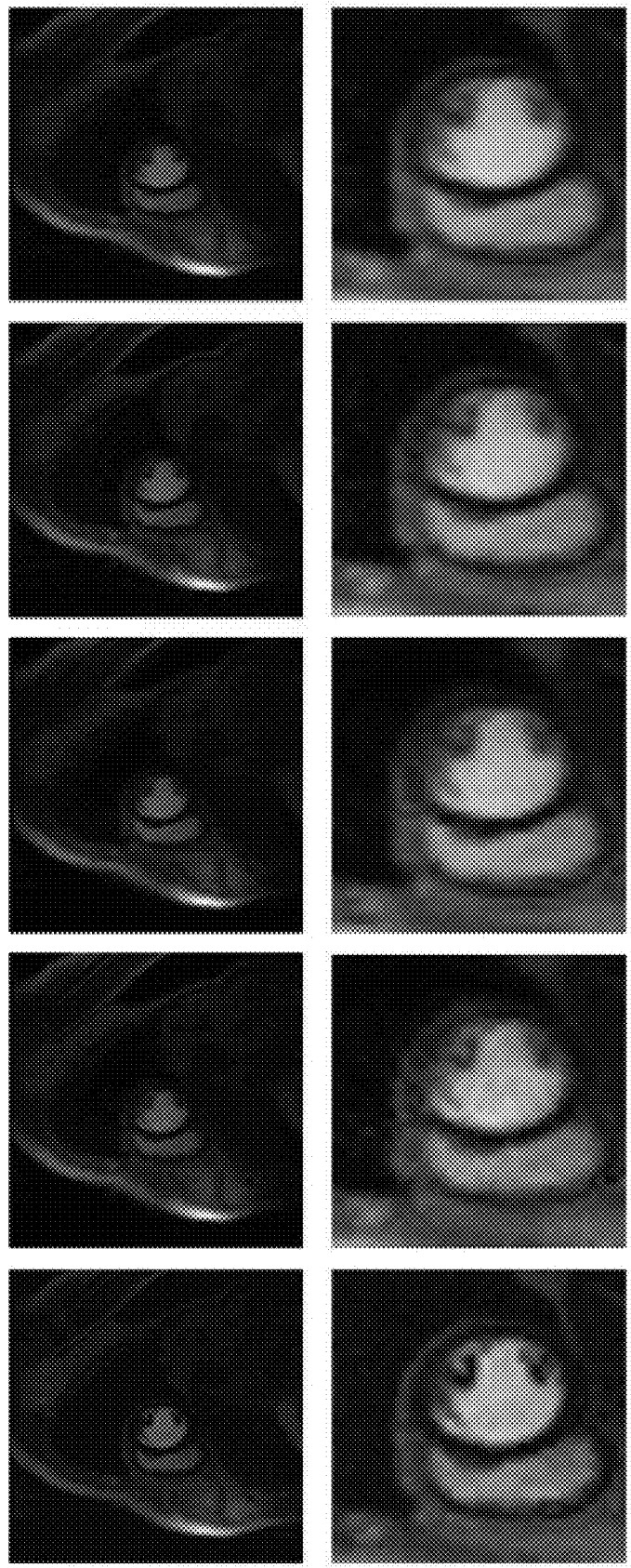
FIG. 5 shows various k-t PCA and k-t SLR reconstructed images of a patient with and without motion compensation using retrospective reconstruction.

FIG. 5 shows various k-t PCA and k-t SLR reconstructed images of a patient with and without motion compensation using retrospective reconstruction. The top row of images shows reconstruction of the entire body cavity of the patient at one time frame, and the bottom row of images shows reconstruction within a heart region of interest at one time frame.

In-Vivo Studies with Prospective Acquisition

Multi-slice 2D saturation-recovery first-pass gadolinium-enhanced data were collected from 10 patients on a 1.5 T scanner using a 5-channel phased-array RF coil. For each patient, 3 short-axis slices were acquired per heartbeat for 50-70 heartbeats. The 4× accelerated variable density k-t sampling pattern fully sampled the central 10 phase-encoding lines while the other 30 phase-encoding lines were undersampled following a Poisson disk distribution. Other parameters included: FOV 320 mm, Matrix 160×160, 40 phase-encoding lines/image, spatial resolution 2 mm×2 mm, slice thickness 8 mm, TR 2.4 ms, saturation recovery time 100 ms, acquisition window per slice 96 ms.

Figure 6:
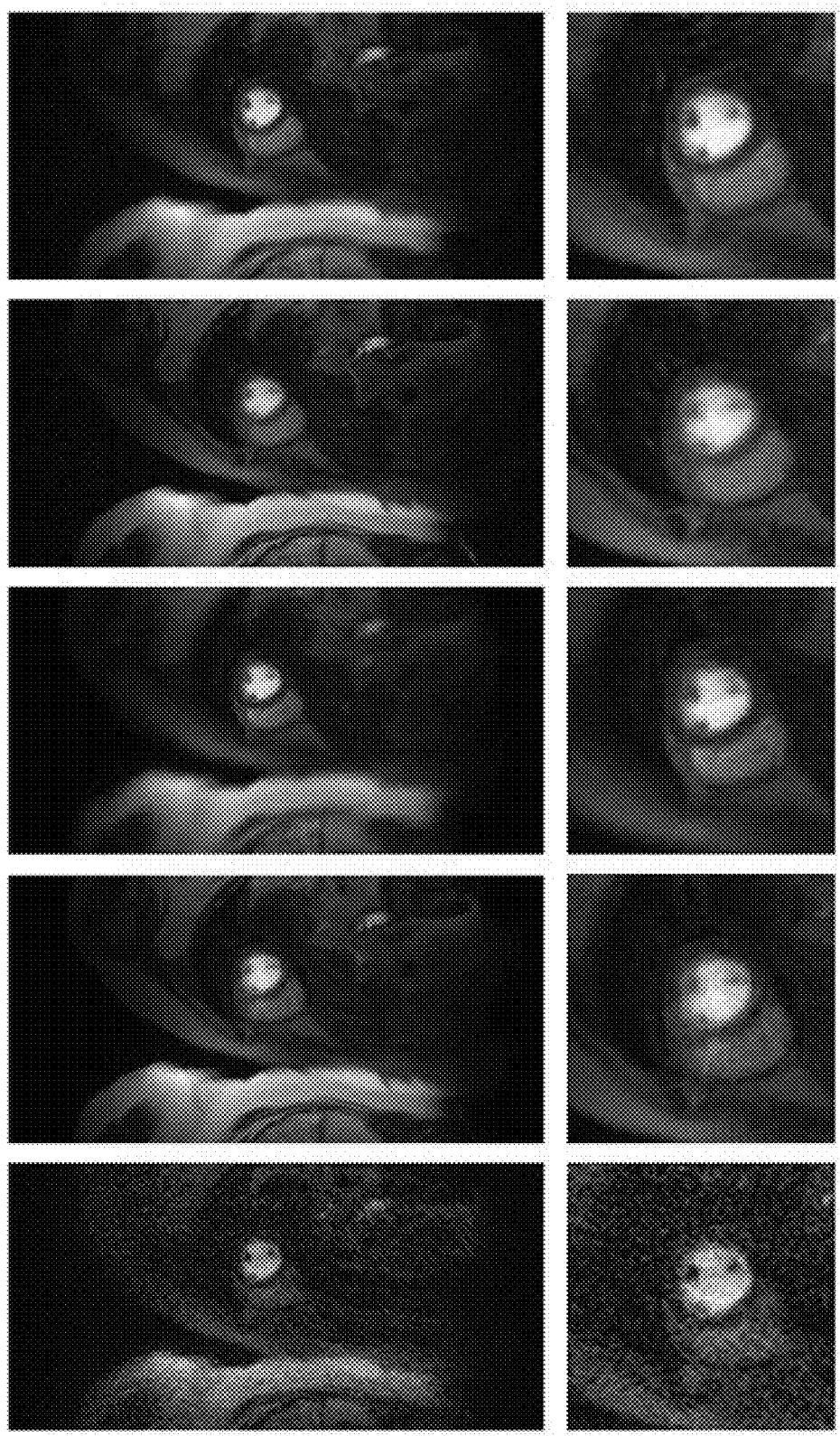
FIG. 6 shows various k-t PCA and k-t SLR reconstructed images of a patient with and without motion compensation using prospective acquisition.

For verification of effectiveness of the motion compensation technique, data was reconstructed using K-t PCA and K-t SLR without motion compensation for comparison of a heart region of interest. FIG. 6 shows various k-t PCA and k-t SLR reconstructed images of a patient with and without motion compensation using prospective acquisition in accordance with one or more example embodiments. Additionally, the images reconstructed using an accelerated imaging technique are compared to SPIRiT reconstructed images, which have extensive motion-induced artifacts. The top row of images shows reconstruction of the entire body cavity of the patient at one time frame, and the bottom row of images shows reconstruction within a heart region of interest at one time frame.

RESULTS

Figure 7:
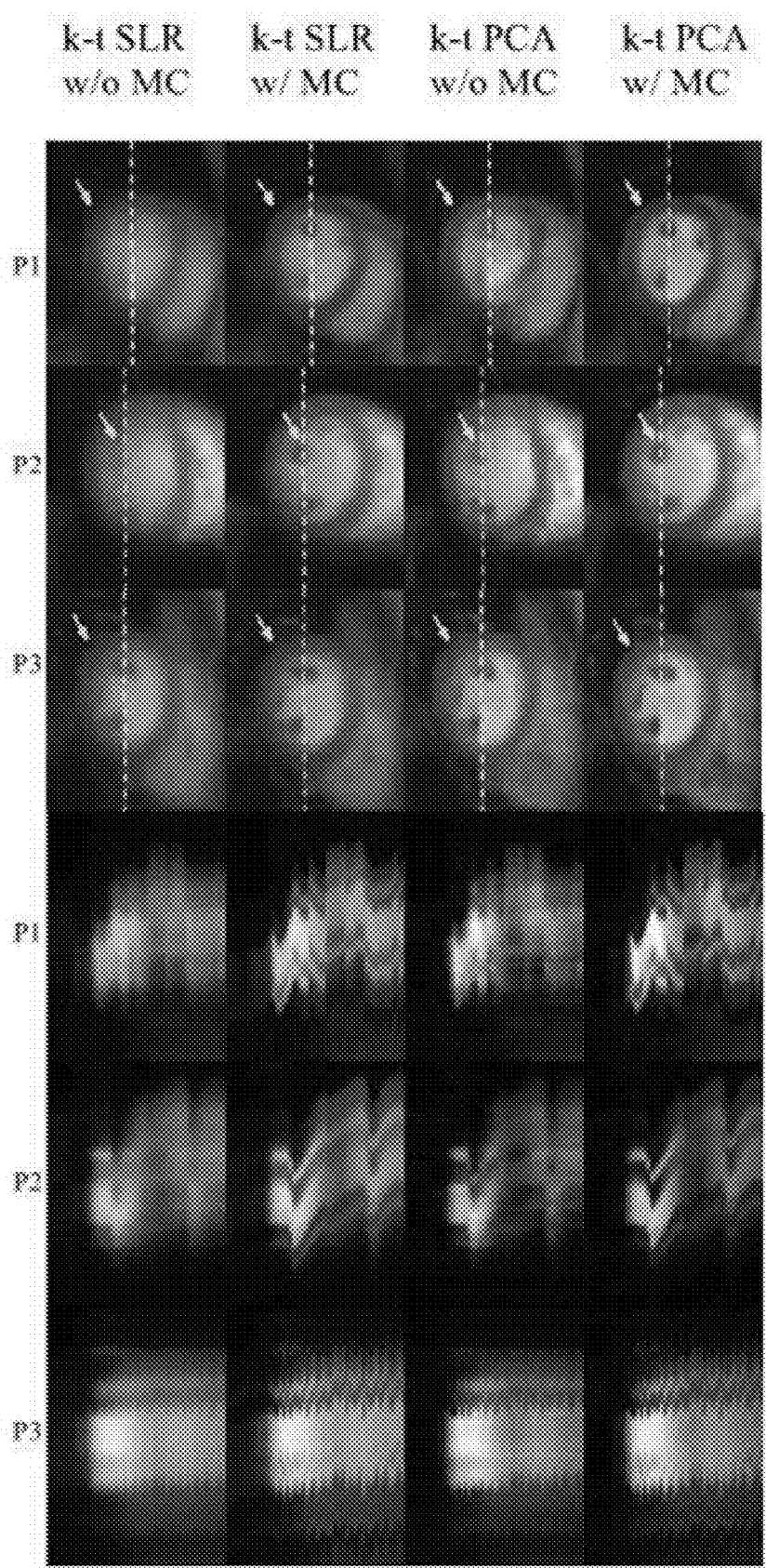
FIG. 7 shows various k-t PCA and k-t SLR reconstructed images of three patients with and without motion compensation, where the patients showed significant respiratory motion during image acquisition.

FIG. 7 shows k-t PCA reconstructed images with and without motion compensation and k-t SLR images with and without motion compensation from three patients with significant respiratory motion during image acquisition. From the images shown in the top three rows in FIG. 7, it can be seen that the reconstructed images using both k-t PCA and k-t SLR with the described motion compensation techniques have much sharper edges and clearly delineated structures within the ventricle that are not well visualized in the non-motion compensated images. From the x-t profiles shown in the bottom three rows in FIG. 7, it can be seen for both patient P1 and patient P2 that the motion artifacts are significantly reduced by the described motion compensation techniques without over-smoothing the temporal signals despite considerable respiratory motion during image acquisition. The respiratory motion of Patient P3 was rapid and shallow during acquisition, but the improvement in image quality is evident in the image reconstruction and in the x-t profiles of the motion corrected images.

DISCUSSION

According to certain implementations of embodiments of the present disclosure, the described motion compensation techniques can, among other advantages and benefits provided, remove respiratory-induced motion artifacts in a heart region of interest. The described motion compensation techniques can remove image artifacts at the expense of some motion degradation of irrelevant anatomy remote from the heart. This property makes the described motion compensation techniques suitable for CMR perfusion imaging, or other CMR applications where the myocardium is the only region of interest, for instance. In cases of multi-phase CMR imaging, such as for cine imaging of heart function, the registration can be performed between images acquired at similar phases of the cardiac cycle, and as such the primary motion corruption will be from respiratory motion. In addition, the described motion compensation techniques improve known methods, limited to non-rigid registration operators, as it only phase-shifts the magnetic resonance data and therefore avoids the spatial blurring associated with repeated application of these non-rigid registration operators. Additionally, some embodiments of motion compensation techniques described herein improve image quality for k-t acceleration (k-t PCA) and compressed sensing (k-t SLR) techniques, typically sensitive to respiratory motion.

CONCLUSION

The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed embodiments, therefore, are considered in all respects to be illustrative and not restrictive. The patentable scope of certain embodiments of the disclosed technology is indicated by the appended claims, rather than the foregoing description, and all changes that come within the meaning and range of equivalents thereof are intended to be embraced therein.

REFERENCE LIST

[1] Pruessmann K P, Weiger M, Scheidegger M B, Boesiger P. SENSE: Sensitivity encoding for fast MRI. Magn Reson Med. 1999; 42:952-62.
[2] Griswold M A, Jakob P M, Heidemann R M, et al. Generalized autocalibrating partially parallel acquisitions (GRAPPA). Magn Reson Med. 2002; 47:1202-10.
[3] Lustig M, Pauly J M. SPIRiT: Iterative self-consistent parallel imaging reconstruction from arbitrary k-Space. Magn Reson Med. 2010; 64(2): 457-71.
[4] Tsao J, Boesiger P, Pruessmann K P. k-t BLAST and k-t SENSE: dynamic MRI with high frame rate exploiting spatiotemporal correlations. Magn Reson Med. 2003; 50(5):1031-42.
[5] Pedersen H, Kozerke S, Ringgaard S, et al. k-t PCA: temporally constrained k-t BLAST reconstruction using principal component analysis. Magn Reson Med. 2009; 62(3):706-16.
[6] Schmidt J F, Wissmann L, Manka R, et al. Iterative k-t principal component analysis with nonrigid motion correction for dynamic three-dimensional cardiac perfusion imaging. Magn Reson Med. 2014; 72(1):68-79.
[7] Lingala S G, Hu Y, DiBella E, et al. Accelerated dynamic MRI exploiting sparsity and low-rank structure: k-t SLR. IEEE Trans Med Imag. 2011; 30(5):1042-54.
[8] Yang Y, Kramer C M, Shaw P W, Meyer C H, Salerno M. First-pass myocardial perfusion imaging with whole-heart coverage using L1-SPIRiT accelerated variable density spiral trajectories. Magn Reson Med. 2016;76(5):1375-87.
[9] Wang Y, Rossman P J, Grimm R C, et al. Navigator-echo-based real-time respiratory gating and triggering for reduction of respiration effects in three-dimensional coronary MR angiography. Radiology. 1996; 198(1):55-60.
[10] Usman M, Atkinson D, Odille F, et al. Motion corrected compressed sensing for free-breathing dynamic cardiac MRI. Magn Reson Med. 2013; 70(2):504-16.
[11] Thevenaz P, Blu T, Unser M. Interpolation revisited. IEEE Trans Med Imaging. 2000; 19:739-58
[12] Wissmann L, Santelli C, Segars W P, et al. MRXCAT: Realistic numerical phantoms for cardiovascular magnetic resonance. J Cardiovasc Magn Reson. 2014; 16:63.

What is claimed is:
1. A method, comprising:
acquiring magnetic resonance data for an area of a subject containing the heart, wherein the acquired magnetic resonance data comprises motion-corrupted data due to respiration of the subject;
reconstructing, from the acquired magnetic resonance data, a preliminary image for each time frame of a plurality of time frames, wherein each time frame corresponds to a single heartbeat of a plurality of heartbeats of the subject and each respective preliminary image is reconstructed independently;
automatically detecting, in the preliminary reconstructed images, a region of interest that consists of a heart region of the subject and that excludes regions of the subject outside the heart region;
performing rigid motion registration on the region of interest in the preliminary reconstructed images to estimate displacement between respective reconstructed images, such that the heart region is aligned across a final reconstructed image series;
determining, based on the estimated displacement from the rigid motion registration, a linear phase shift for motion correction;
applying the linear phase shift to the acquired magnetic resonance data with the motion-corrupted data to produce linear phase-shifted data; and
performing a k-t image reconstruction on the linear phase-shifted data to produce a time series of images in which the region of interest is motion-corrected for the final reconstructed image series.

2. The method of claim 1, wherein each respective image is reconstructed independently such as to avoid temporal blurring in images used for image registration.

3. The method of claim 1, wherein reconstructing, from the acquired magnetic resonance data, a preliminary image for each time frame of a plurality of time frames uses parallel image reconstruction.

4. The method of claim 3, wherein the parallel image reconstruction comprises iterative self-consistent parallel image reconstruction (SPIRiT).

5. The method of claim 1, wherein performing rigid motion registration on the region of interest in the preliminary reconstructed images comprises performing registration in the image domain or k-space domain.

6. The method of claim 1, wherein determining, based on the rigid registration, the linear phase shift comprises deriving linear k-space shifts in the x and y direction.

7. The method of claim 1, wherein acquiring the magnetic resonance data comprises performing k-t accelerated acquisition.

8. The method of claim 1, wherein performing the k-t image reconstruction on the linear phase-shifted data comprises k-t exploiting sparsity and low rank structure (k-t SLR), k-t principal component analysis (k-t PCA), or k-t PCA with sensitivity encoding (SENSE).

9. The method of claim 1, wherein the magnetic resonance data is acquired during free-breathing of the subject or continuous data acquisition in multiple phases of the cardiac cycle of the heart of the subject.

10. The method of claim 1, wherein the magnetic resonance data is acquired using a Cartesian, radial, or spiral k-space trajectory.

11. The method of claim 1, wherein acquiring the magnetic resonance data comprises incoherent sampling and the k-t image reconstruction comprises compressed sensing reconstruction exploiting sparsity in the temporal direction.

12. A system, comprising:

a data acquisition device configured to acquire magnetic resonance data for an area of a subject containing the heart, wherein the acquired magnetic resonance data comprises motion- corrupted data due to respiration of the subject; and one or more processors coupled to the data acquisition device and configured to cause the system to perform functions including:

reconstructing, from the acquired magnetic resonance data, a preliminary image for each time frame of a plurality of time frames, wherein each time frame corresponds to a single heartbeat of a plurality of heartbeats of the subject and each respective preliminary image is reconstructed independently;

automatically detecting, in the preliminary reconstructed images, a region of interest that consists of a heart region of the subject and that excludes regions of the subject outside the heart region;

performing rigid motion registration on the region of interest in the preliminary reconstructed images to estimate displacement between respective reconstructed images, such that the heart region is aligned across a final reconstructed image series;

determining, based on the estimated displacement from the rigid motion registration, a linear phase shift for motion correction;

applying the linear phase shift to the acquired magnetic resonance data with the motion-corrupted data to produce linear phase-shifted data; and performing a k-t image reconstruction on the linear phase-shifted data to produce a time series of images in which the region of interest is motion-corrected for the final reconstructed time series.

13. The system of claim 12, wherein each respective preliminary image is reconstructed independently such as to avoid temporal blurring in images used for image registration.

14. The system of claim 12, wherein reconstructing, from the acquired magnetic resonance data, a reconstructed image for each time frame of a plurality of time frames uses parallel image reconstruction.

15. The system of claim 14, wherein the parallel image reconstruction comprises iterative self-consistent parallel image reconstruction (SPIRiT).

16. The system of claim 12, wherein performing rigid motion registration on the region of interest in the preliminary reconstructed images comprises performing registration in the image domain or k-space domain.

17. The system of claim 12, wherein determining, based on the rigid registration, the linear phase shift comprises deriving linear k-space shifts in the x and y direction.

18. The system of claim 12, wherein acquiring the magnetic resonance data comprises performing k-t accelerated acquisition.

19. The system of claim 12, wherein performing the k-t image reconstruction on the linear phase-shifted data to produce motion corrected images comprises k-t exploiting sparsity and low rank structure (k-t SLR), k-t principal component analysis (k-t PCA), or k-t PCA with sensitivity encoding (SENSE).

20. The system of claim 12, wherein the magnetic resonance data is acquired during free-breathing of the subject or continuous data acquisition in multiple phases of the cardiac cycle of the heart of the subject.

21. The system of claim 12, wherein the magnetic resonance data is acquired using a Cartesian, radial, or spiral k-space trajectory.

22. The system of claim 12, wherein acquiring the magnetic resonance data comprises incoherent sampling and the k-t image reconstruction comprises compressed sensing reconstruction exploiting sparsity in the temporal direction.

23. A non-transitory computer-readable medium having stored instructions that, when executed by one or more processors, cause a computing device to perform functions that comprise:

acquiring magnetic resonance data for an area of a subject containing the heart, wherein the acquired magnetic resonance data comprises motion-corrupted data due to respiration of the subject;

reconstructing, from the acquired magnetic resonance data, a preliminary image for each time frame of a plurality of time frames, wherein each time frame corresponds to a single heartbeat of a plurality of heartbeats of the subject and each respective preliminary image is reconstructed independently;

automatically detecting, in the preliminary reconstructed images, a region of interest that consists of a heart region of the subject and that excludes regions of the subject outside the heart region;

performing rigid motion registration on the region of interest in the preliminary reconstructed images to estimate displacement of the heart region between respective reconstructed images, such that the heart region is aligned across a final reconstructed image series;

determining, based on the estimated displacement from the rigid motion registration, a linear phase shift for motion correction;

applying the linear phase shift to the acquired magnetic resonance data with the motion- corrupted data to produce linear phase-shifted data; and performing a k-t image reconstruction on the linear phase-shifted data to produce a time series of images in which the region of interest is motion-corrected images for the final reconstructed image series.

* * * * *